(12) United States Patent
Urban et al.

(10) Patent No.: US 9,377,343 B2
(45) Date of Patent: Jun. 28, 2016

(54) APPARATUS FOR DETERMINING AND/OR MONITORING A PREDETERMINED FILL LEVEL

(75) Inventors: Martin Urban, Lorrach (DE); Helmut Pfeiffer, Steinen (DE); Volker Dreyer, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 587 days.

(21) Appl. No.: 13/811,812

(22) PCT Filed: Jun. 20, 2011

(86) PCT No.: PCT/EP2011/060195
§ 371 (c)(1),
(2), (4) Date: Jan. 23, 2013

(87) PCT Pub. No.: WO2012/013422
PCT Pub. Date: Feb. 2, 2012

(65) Prior Publication Data
US 2013/0118254 A1    May 16, 2013

(30) Foreign Application Priority Data
Jul. 28, 2010   (DE) .......................... 10 2010 038 535

(51) Int. Cl.
| | |
|---|---|
| *G01F 23/26* | (2006.01) |
| *G01F 23/24* | (2006.01) |
| *G01F 23/296* | (2006.01) |
| *G01F 25/00* | (2006.01) |

(52) U.S. Cl.
CPC .............. *G01F 23/266* (2013.01); *G01F 23/24* (2013.01); *G01F 23/268* (2013.01); *G01F 23/2968* (2013.01); *G01F 25/0061* (2013.01)

(58) Field of Classification Search
CPC ..... G01F 23/24; G01F 23/268; G01F 23/266; G01F 25/0061; G01F 23/2968
USPC ............ 73/304 C, 1.73, 290 V, 304 R, 290 R, 73/64.53
See application file for complete search history.

(56) References Cited

U.S. PATENT DOCUMENTS

| | | | |
|---|---|---|---|
| 4,347,741 A | * | 9/1982 | Geiger ......................... 73/304 C |
| 4,568,874 A | * | 2/1986 | Kramer et al. ................. 324/688 |

(Continued)

FOREIGN PATENT DOCUMENTS

| | | |
|---|---|---|
| CN | 1110402 A | 10/1995 |
| DE | 3215040 A1 | 11/1983 |

(Continued)

OTHER PUBLICATIONS

German Search Report, Jul. 28, 2010, Munich.

(Continued)

*Primary Examiner* — Hezron E Williams
*Assistant Examiner* — Marrit Eyassu
(74) *Attorney, Agent, or Firm* — Bacon & Thomas, PLLC

(57) ABSTRACT

An apparatus for determining and/or monitoring at least one fill level of a medium in a container comprising: a capacitive or conductive probe unit having at least one electrode; and a control/evaluation unit. The electrode is a hollow body, that an end region of the electrode protruding into the container is embodied as an oscillatable membrane. On an inner side of the membrane a driving/receiving unit is arranged, which excites the membrane to execute mechanical oscillations and receives mechanical oscillations therefrom and converts such into an electrical, received signal. The control/evaluation unit supplies the electrode at least at times with a voltage and determines the fill level of the medium capacitively or conductively, and/or that the control/evaluation unit supplies the driving/receiving unit at least at times with an exciter signal and determines from the electrical received signal the fill level of the medium.

9 Claims, 1 Drawing Sheet

(56) References Cited

U.S. PATENT DOCUMENTS

| | | | |
|---|---|---|---|
| 4,594,891 A | | 6/1986 | Benz |
| 5,099,454 A | * | 3/1992 | Dieulesaint ......... G01F 23/2961 |
| | | | 340/621 |
| 5,524,486 A | * | 6/1996 | Hermann ............ G01F 23/2967 |
| | | | 73/290 V |
| 5,966,983 A | * | 10/1999 | Pfeiffer ............... G01F 23/2961 |
| | | | 73/291 |
| 6,920,787 B2 | * | 7/2005 | Brutschin et al. ........... 73/290 V |
| 6,946,779 B2 | * | 9/2005 | Birgel ........................... 310/366 |
| 2006/0142954 A1 | * | 6/2006 | Muller et al. .................. 702/30 |

FOREIGN PATENT DOCUMENTS

| | | | |
|---|---|---|---|
| DE | 4126399 A1 | | 2/1993 |
| DE | 4308996 A1 | | 10/1994 |
| DE | 10051025 A1 | | 4/2002 |
| DE | 20320382 U1 | | 7/2004 |
| DE | 102004045765 A1 | * | 4/2006 |
| DE | 102004045765 A1 | | 4/2006 |
| FR | 2 265 084 | | 10/1975 |
| WO | WO 03/052360 A1 | | 6/2003 |

OTHER PUBLICATIONS

International Search Report, Nov. 25, 2011, The Netherlands.

German Search Report dated Feb. 3, 2011, issued in Application No. 10 2010 038 535.2 in Munich, Germany.

International Preliminary Report on Patentability dated Feb. 7, 2013, issued in Application No. PCT/EP2011/060195 in Geneva, Switzerland.

* cited by examiner

APPARATUS FOR DETERMINING AND/OR MONITORING A PREDETERMINED FILL LEVEL

TECHNICAL FIELD

The present invention relates to an apparatus for determining and/or monitoring at least one fill level of a medium in a container. The apparatus at least comprises: a capacitive or conductive probe unit having at least one electrode; and a control/evaluation unit.

BACKGROUND DISCUSSION

For determining or monitoring a limit level of a medium in a container, various measuring devices are known, which operate according to different measuring principles, wherein the choice of the measuring device depends on the respective field of application. For example, for conductive liquids, preferably conductive sensors are used, in the case of which the resistance between a rod electrode provided in the container and the container wall is measured. For media with a low conductivity, conductive measuring is, however, difficult or even impossible. In the case of non-conducting liquids, frequently capacitive sensors are used, which likewise have one or more electrodes and which determine the capacitance between an electrode and the container wall. The medium acts as the dielectric in such case. Independently of the conductivity of a liquid, vibronic limit level switches in the form of membrane oscillators or oscillatory forks can be applied, which detect the medium based on changed oscillation characteristics of an element excited to oscillate. Vibronic limit level switches can, however, deliver defective measurement results in the case of high viscosity or outgassing media. A measuring device equally suitable for all these applications is so far not known.

SUMMARY OF THE INVENTION

An object of the invention is thus to provide a fill level measurement apparatus with an increased application bandwidth.

The object is achieved by features including that the electrode is embodied as a hollow body, that an end region of the electrode protruding into the container is embodied as an oscillatable membrane, that on an inner side of the membrane a driving/receiving unit is arranged, which excites the membrane to execute mechanical oscillations and receives mechanical oscillations therefrom and converts such into an electrical, received signal, and that the control/evaluation unit supplies the electrode at least at times with a voltage and determines the fill level of the medium capacitively or conductively, and/or that the control/evaluation unit supplies the driving/receiving unit at least at times with an exciter signal and determines from the electrical received signal the fill level of the medium.

The probe unit is thus not only able to perform capacitive or conductive fill level measurement, but, instead, supplementally, can determine the fill level vibronically. In this way, the process variable, limit-level, can be determined redundantly in independent manner, so that an ability to check the information concerning the fill level is created. If one of two measuring principles fails, it can still be assured, by measuring with the other principle, that the fill level is correctly determined and displayed. This increases the safety of a system for fill-level monitoring. Furthermore, it is possible with the apparatus to determine other process variables, such as viscosity and/or density of the medium. Thus, also a multifunctional, or multivariable, sensor is provided.

The fill level is preferably continually determined by means of two measuring methods. On the other hand, in applications with changing process conditions, the measuring principles can be switched between and the measuring method best suited for the respective conditions used. Due to its multifaceted opportunities for use, the measuring device can be procured earlier and stored, without having to know the media properties at the later location of use.

Furthermore, there is the opportunity to retrofit existing vibronic measuring devices with one or more electrodes insulated from one another, in order so to enable the additional capacitive or conductive measuring. The vibronic measuring device can, in such case, be equally a membrane oscillator, an oscillatory fork or a single rod oscillator.

In a first embodiment of the solution of the invention, the control/evaluation unit determines the capacitance or the electrical resistance between the electrode and a wall of the container and ascertains the fill level therefrom. In the conductive measuring, an alternating voltage is placed on the electrode, the container grounded and the resistance between electrode and container, or the electrical current flow, determined. When the conductive medium is in contact with the probe unit, an electrical current, or resistance, is measured. In the capacitive measuring of the fill level of a non-conductive medium, the medium forms a dielectric, which is arranged between the capacitor plates formed by the electrode and the grounded wall of the container.

In an embodiment, the probe unit includes insulation, which, at least sectionally, radially surrounds the electrode. The insulation serves, on the one hand, for protecting the electrode against corrosion and, on the other hand, for electrical insulation between the electrode and a conductive medium. In the capacitive determining of fill level of a conductive medium, the insulation serves as dielectric and the medium, instead of the container, as counter electrode.

In an embodiment, the apparatus includes at least a second electrode. The electrode embodied as a hollow body can then be referred to as the first electrode. In a therewith connected, additional embodiment, the second electrode surrounds the first electrode and the insulation at least sectionally coaxially. The second electrode can essentially have the same length as the first electrode, or be shorter, and surround the first electrode only in a portion neighboring the process connection. Preferably, the second electrode is supplied with the same voltage as the first electrode and serves as shielding electrode, in order to prevent measurement error in the case of accretion formation. In an alternative embodiment for capacitive determining of the fill level of a non-conductive liquid, the second electrode surrounds the first electrode coaxially, wherein medium can penetrate between the first and second electrodes. The second electrode serves then as grounding tube and the capacitance measurement takes place between the two electrodes instead. In the case of a conductive probe, the electrical current can be measured between, in each case, an electrode and ground. The two measured values are then compared for evaluation. In another embodiment of a conductive probe unit, the second electrode forms the ground.

An embodiment of the apparatus includes the feature that the probe unit is arranged flushly mounted in the container. This embodiment offers the advantage that the probe unit offers no site for accumulation of dirt and germs, since only the end region of the probe unit comes in contact with the medium. In this embodiment, only a limit-level is monitorable with the conductive or capacitive measuring.

In an alternative embodiment, the probe unit is rod-shaped and protrudes completely into the container. Associated with this is another embodiment of the apparatus, in the case of which the second electrode is arranged spaced and electrically insulated from the first electrode. If the container containing the medium is non-conducting, the second rod-shaped electrode serves as ground for the conductive or capacitive measuring. In an embodiment, the second electrode and the first electrode are differently long, so that a minimum and a maximum fill level are conductively detectable. In an additional embodiment, the probe unit includes, besides the first electrode, a second and a third electrode, wherein the first and second electrodes are differently long and serve for monitoring two different fill levels and wherein the third electrode forms the ground, instead of the container.

In an embodiment of the invention, the driving/receiving unit comprises at least one piezoelectric element. In such case, it is a stack drive of a plurality of piezoelectric elements arranged on top of one another or a bimorph drive of one piezoelectric element or a plurality of elements arranged directly on the membrane.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
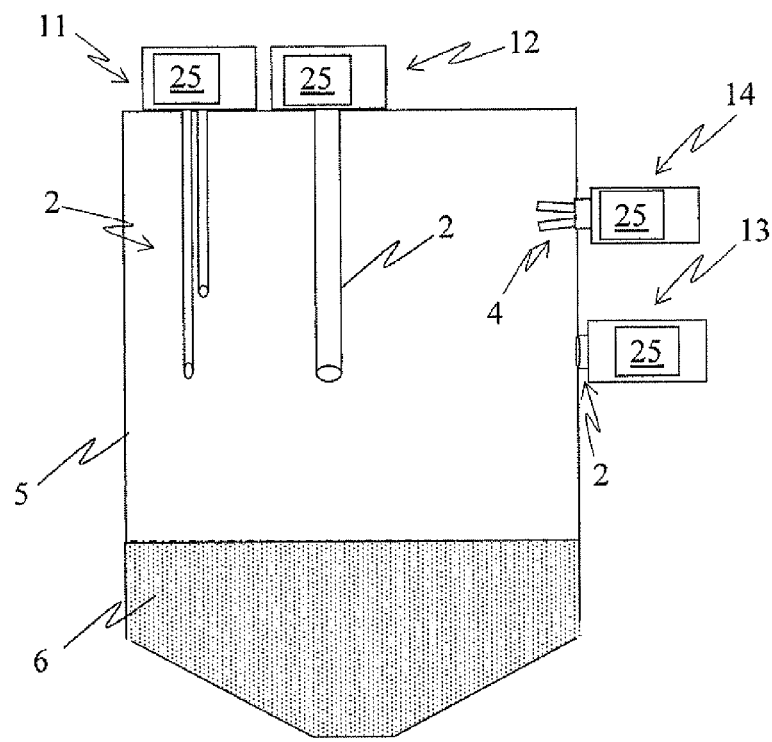
FIG. 1 schematically, various fill level measuring devices in a container.

FIG. 1 shows a container 5 partially filled with a liquid medium 6 and having four different measuring devices for monitoring a fill level. Shown are a conductive sensor 11, a capacitive sensor 12, a flush sensor 13, which measures capacitively or conductively, and an oscillatory fork 14 as representative of a vibronic measuring device. The measuring devices 11, 12 have, in each case, a probe unit 2, which protrudes from above inwardly into the container 5. The electronic components, such as the control/evaluation unit 25, are accommodated in a sensor head, which remains outside of the container. The probe unit 2 of the flush mounting sensor 13 installed laterally in the container ends flushly with the wall of the container 5, so that only a surface is present in the interior of the container 5. Each of the probe units 2 has one or more electrodes and serves for capacitive or conductive registering of fill level. Such measuring devices are known from the state of the art and are available from Endress+Hauser in a large variety of models. The invention concerns itself equally with flush probe units, rod probes and cable probes, in the case of which the probe unit is secured to a cable. Furthermore, the invention relates to vibronic measuring devices, i.e. so called oscillatory forks, single oscillatory rods and membrane oscillators. An oscillatory fork 14 is shown as an example of a vibronic measuring device. Oscillatory fork 14 possesses an oscillatable unit 4, which is excited to execute oscillations. The oscillation characteristics depend on the density of the medium, so that, from these, the degree of covering with medium, as well as, in the immersed state, density and viscosity of the medium are determinable.

Figure 2:
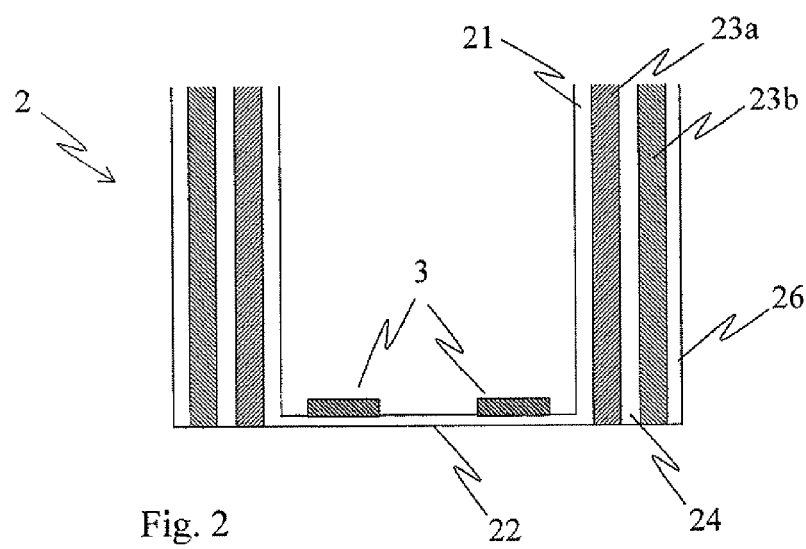
FIG. 2 a schematic probe structure.

FIG. 2 shows an advantageous embodiment of an apparatus of the invention using the example of a flush mounting, capacitive sensor 13 for use in a non- or only very slightly conductive media. This is arranged in the container 5 at the height corresponding to the fill level to be monitored. Shown is a section through the end region of the cylindrical probe unit 2. The outer construction corresponds to that of usual flush capacitive probe units: the structure is encapsulated by a housing 26, which also serves as a process connection, for example, by being provided with threading for engagement with a container 5. Concentrically arranged are a first electrode 21 and a second electrode 24, as well as two insulations 23a, 23b, wherein the inner insulation 23a insulates the first electrode 21 electrically from the second electrode 24, and wherein the outer insulation 23b insulates the second electrode 24 electrically from the housing 26. The housing 26 is grounded, while the first electrode 21 and the second electrode 24 are supplied with the same alternating voltage. The second electrode 24 serves as guard- or shielding electrode, while with the cylindrical, first electrode 21 the fill level of the medium 6 is determined via the capacitance between the first electrode 21 and the wall of the container 5, or the housing 26. Preferably, the electrodes 21, 24 and the housing 26 are manufactured of stainless steel.

In contrast to usual measuring electrodes, the first electrode 21 is a hollow body. The lateral surfaces facing the medium 6, respectively the interior of the container 5, are embodied as the two sides of a thin membrane 22, which is oscillatable. On the inner side of the membrane 22, i.e. on the surface lying in the interior of the probe unit 2, are symmetrically arranged two piezoelectric elements as driving/receiving unit 3. In other embodiments, the driving/receiving unit 3 is composed of only one piezoelectric element or of a plurality of piezoelectric elements arranged in a stack. The position of the driving/receiving unit 3 on the membrane 22 depends essentially on the oscillatory mode to be produced. Upon applying an electrical alternating voltage to the driving/receiving unit 3, it excites the membrane 22 to execute mechanical oscillations. The excitation occurs, in such case, such that the membrane 22 oscillates in an eigenmode. With the illustrated arrangement, for example, the first eigenmode can be excited, i.e. one half of the membrane oscillates with opposite phase to the other half. If the degree of covering of the membrane 22 with medium 6 changes, then also the oscillation frequency changes, so that the reaching of the fill level is detectable therefrom. Furthermore, with the information won from the capacitive measuring concerning the fill level, from the information won with the vibronic measuring concerning the oscillation characteristics, the density or the viscosity of the medium 6 is determinable. The determining of fill level, density and viscosity by means of the oscillations of the membrane 22 occurs analogously to known methods of vibronic measuring with membrane oscillators.

The shown construction corresponds, moreover, also to that of a flush mounting, conductive probe for determining a limit level of a conductive medium.

In another approach, a membrane oscillator or an oscillatory fork is equipped with at least one supplemental insulated electrode, so that likewise a construction according to FIG. 2 results. In this case, the housing of the membrane oscillator, or the housing of the oscillatory fork, whose end region is formed by the membrane 22, or the membrane with thereon arranged fork tines, forms the first electrode 21.

With the probe unit 2 embodied according to the invention, the fill level can, thus, be determined in two ways; vibronically and capacitively, or vibronically and conductively. Common to all embodiments is that two completely different measuring principles are involved, respectively the measuring is based on completely different properties of the medium. These are, in the case of the conductive measuring, the conductivity, in the case of the capacitive measuring, the dielectric constant, and in the case of the vibronic measuring, the density of the medium. In this way, the measurements can be combined in a shared function range for an especially reliable measuring, and, moreover, cover, individually, measuring ranges, which are not attainable with the, respectively, other measuring principle. In this way, supplementally, the application bandwidth is increased. The disadvantage of the problem burdened measuring upon the occurrence of air bubbles in the medium for a membrane oscillator is compensated by the fact that a capacitive or conductive measuring is possible uninfluenced by air bubbles. The disadvantage of the conductive measuring principle, wherein measuring in media with very small conductances is not possible, is compensated by the independence of vibronic measuring from the conductivity of the medium.

The invention claimed is:

1. An apparatus for determining and/or monitoring at least one fill level of a medium in a container, comprising:
a capacitive or conductive probe unit having at least one electrode; and
a control/evaluation unit, wherein:
said at least one electrode is embodied as a hollow body, with an end region protruding into the container and embodied as an oscillatable membrane, on an inner side of which a driving/receiving unit is arranged, which excites said oscillatable membrane to execute mechanical oscillations and receive mechanical oscillations therefrom and convert such into an electrical, received signal;
said control/evaluation unit supplies said at least one electrode at least at times with a voltage and determines the fill level of the medium capacitively or conductively; and/or
said the control/evaluation unit supplies said driving/receiving unit at least at times with an exciter signal and determines from the electrical received signal the fill level of the medium.

2. The apparatus as claimed in claim 1, wherein:
said control/evaluation unit ascertains the fill level from the capacitance or the electrical resistance between said at least one electrode and a wall of the container.

3. The apparatus as claimed in claim 1, wherein:
said probe unit includes insulation, which, at least sectionally, radially surrounds said at least one electrode.

4. The apparatus as claimed in claim 1, further comprising:
at least a second electrode.

5. The apparatus as claimed in claim 4, wherein:
said at least a second electrode surrounds said at least a first electrode and an insulation coaxially.

6. The apparatus as claimed in claim 4, wherein:
said at least said second electrode is arranged spaced and electrically insulated of said at least said first electrode.

7. The apparatus as claimed in claim 1, wherein:
said probe unit is arranged flushly mounted in the container.

8. The apparatus as claimed in claim 1, wherein:
said probe unit is rod-shaped and protrudes completely into the container.

9. The apparatus as claimed in claim 1, wherein:
said driving/receiving unit comprises at least one piezoelectric element.

* * * * *